United States Patent
Moore et al.

(10) Patent No.: US 11,565,989 B2
(45) Date of Patent: Jan. 31, 2023

(54) SEPARATION, RECOVERY AND UPGRADING OF BIOMASS DERIVED 2,3-BUTANEDIOL

(71) Applicant: U.S. Department of Energy, Washington, DC (US)

(72) Inventors: Cameron Moore, Los Alamos, NM (US); Trideep Rajale, Los Alamos, NM (US); Karthikeyan K. Ramasamy, Richland, WA (US); Andrew Sutton, Los Alamos, NM (US)

(*) Notice: Subject to any disclaimer, the term of this patent is extended or adjusted under 35 U.S.C. 154(b) by 128 days.

(21) Appl. No.: 17/087,841

(22) Filed: Nov. 3, 2020

(65) Prior Publication Data

US 2022/0135507 A1    May 5, 2022

(51) Int. Cl.
*C07C 29/92* (2006.01)
*C07C 31/20* (2006.01)

(52) U.S. Cl.
CPC ............ *C07C 29/92* (2013.01); *C07C 31/207* (2013.01); *C07C 2521/12* (2013.01); *C07C 2531/025* (2013.01)

(58) Field of Classification Search
CPC ... C07C 29/92; C07C 31/207; C07C 2521/12; C07C 2531/025
See application file for complete search history.

(56) References Cited

U.S. PATENT DOCUMENTS 2,406,713 A * 8/1946 Senkus .................. C07C 29/88
549/430
2014/0238841 A1 * 8/2014 Kawamura ............... C12P 7/16
203/29

FOREIGN PATENT DOCUMENTS

CN          102154384 B * 3/2013 ............... C12P 7/18

OTHER PUBLICATIONS

CN 102154384, Wang, Y. et al, Method for producing chiral pure (2S,3S)-2,3-butanediol, English translation,9 pages (Year: 2013).*
Li, Y. et al., Separating 2,3-butanediol from fermentation broth using n-butylaldehyde, Journal of Saudi Chemical Society, 20, S495-S502 (Year: 2016).*
Staples, O. et al., A simple solvent free method for transforming bio-derived aldehydes into cyclic acetals for renewable diesel fuels, Sustainable Energy & Fuels, 2, 2742-2746 (Year: 2018).*

* cited by examiner

*Primary Examiner* — Yate' K Cutliff
(74) *Attorney, Agent, or Firm* — Carmen Ekstrom; James Durkis; Brian Lally

(57) ABSTRACT

The invention relates to a two-way approach to isolate, recover and upgrade 2,3-Butanediol (2,3-BDO) from fermentation broth. A complete separation and recovery process for 2,3-BDO using acetalization and trans-acetalization sequence. Acetalization with butyraldehyde using heterogeneous catalysts, either Amberlyst-15® or Nafion NR50®, efficiently isolates 2,3-BDO as phase-separated protected dioxolane. The approach provides significant process advantages with easy product recovery and high recyclability of the catalyst. Trans-acetalization of dioxolane with methanol (methanolysis) followed by distillation of acetal, yielded very high purity 2,3-BDO with about 90% isolated yield. Alternatively, dioxolane is used in a process direct to methyl ethyl ketone (MEK) as a BDO synthon allowing for recovery of the aldehyde.

20 Claims, 6 Drawing Sheets

Scheme 1

FIGURE 1B Scheme 1

SEPARATION, RECOVERY AND UPGRADING OF BIOMASS DERIVED 2,3-BUTANEDIOL

GOVERNMENT SUPPORT

This invention was made with government support under Prime Contract No. DE-AC52-06NA252396 awarded by the U.S. Department of Energy. The government has certain rights in the invention.

FIELD OF THE INVENTION

The present invention relates, generally, to the separation, recovery and upgrading of biomass derived 2, 3-butanediol (2,3-BDO). The invention relates to catalytic conversion of 2,3-BDO from fermentation broth. More particularly, to catalytic conversion effected by heterogeneous catalysts selected from Nafion NR50® and Amberlyst 15®.

BACKGROUND OF THE INVENTION 2,3-Butanediol (2,3-BDO) is a valuable bio-based chemical that has wide range of industrial applications. Especially, derivatives of 2,3-BDO find applications as plasticizers, cosmetics, drugs, polymers, and food additives. Considered as promising platform molecule, 2,3-BDO is used for the synthesis of basic and fine chemicals such as dehydration products methyl ethyl ketone (MEK) and butadiene. Moreover, it also has application as a sustainable and renewable drop-in fuel due to its high anti-knock index and high heating value (27.19 KJ $g^{-1}$).

Currently, the global 2,3-BDO market is valued at 75 million USD, and with wide applications of 2,3-BDO and its derivatives the overall production and demand is expected to surge. According to QY research report published recently, nearly 15,000 MT (metric ton) of 2,3-BDO was produced globally in 2019, and the overall compound annual growth rate is expected to increase to 2.88% by 2025. Several metabolic engineering fermentation processes were developed to enhance the production of BDO. Recently, Zhang and coworkers reported an efficient metabolic pathway using engineered *Zymomonas* strains (*Zymomonas mobilis*) for large scale product of 2,3-BDO, up to 120 g/L. However, the separation and recovery of BDO from the complex fermentation broth remains a challenge due to its aqueous solubility. The current process involves water removal and distillation of 2,3-BDO (boiling point 180° C.) from the fermentation mixture. The high thermal energy required makes the process less economical and high energy intensive. This traditional approach also concentrates the other broth components, as well as 2,3-BDO, which makes downstream processing more challenging. Several other methods reported include liquid-liquid extraction, pervaporation (membrane separation), anionic extraction, sugaring-out extraction etc. In addition to these, recent reports also suggested butanol-based extraction-assisted distillation for purification of 2,3-BDO.

However, these methods are hampered by inherent limitations and drawbacks; such as membrane fouling caused by other broth components, a large excess of solvent used and low 2,3-BDO isolated yields. Reactive extraction methods possess several advantages over distillation including large throughput and low energy consumption. Earlier reports of reactive extraction methodology for isolation of 2,3-BDO uses strongly acidic environment that are corrosive and would require advanced alloys or coatings in plant equipment which may prove impractical and costly. Heterogeneous catalysts hold significant advantages over conventional homogeneous catalysts. When employed in an industrial setting, easy separation of products from reaction medium, recycling and reuse of heterogeneous catalysts makes the process economical and environmentally friendly.

The present inventors have reported a simple, solvent free method for the acetalization of 2,3-BDO with bio-derived aldehydes to yield substituted 1,3-dioxolanes (cyclic acetal). Phase separation and easy isolation of high purity dioxolanes. Thus, eliminating elaborate purification processes which is a major advantage of the present method. The present invention provides the separation and recovery of 2,3-BDO from fermentation broth as an acetal (dioxolane). Upon coordination to form cyclic acetals (dioxolane), the product phase separates from the 2,3-BDO/water mixture and can readily be isolated as the pure compound. The present inventors have also investigated the conversion of dioxolane (as a 2,3-BDO synthon) to the synthetically important dehydration product, methyl ethyl ketone. The cyclic acetal (dioxolane) produced from the reaction between butyraldehyde and BDO was utilized to demonstrate the butyraldehyde recyclability and the conversion of BDO to fuels (precursor).

Two different approaches can be utilized to recover the butyraldehyde and BDO or its derivatives for fuel(s) generation from dioxolane. These are: 1) hydrolyze the dioxolane to generate butyraldehyde and BDO and 2) cleave the dioxolane to generate butyraldehyde and methyl ethyl ketone (MEK).

It is an object of the present invention to provide a method for the separation, recovery and upgrading of biomass derived 2,3-BDO. The present method overcomes the current drawbacks of available processes, as well as, problems associated with recovering 2,3-BDO in low yields and purity.

SUMMARY OF THE INVENTION

The present invention is directed to a method for a complete separation and recovery process for 2,3-BDO using acetylation and trans-acetylation sequence. Acetalization with an aldehyde in the presence of a heterogeneous catalyst forming cyclic acetal (dioxolane). Trans-acetylation of dioxolane with methanol (methanolysis) followed by distillation of acetal yielding high purity 2,3-BDO with at least 90% isolated yield. The dioxolane is cleaved to obtain methyl ethyl ketone (MEK) and butanal (butyraldehyde). Recycling butanal by adding the resulting product of MEK and butanal to the fermentation broth.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1B (Scheme 1) BDO separation and recovery strategy.

DETAILED DESCRIPTION OF THE INVENTION

Figure 1A:
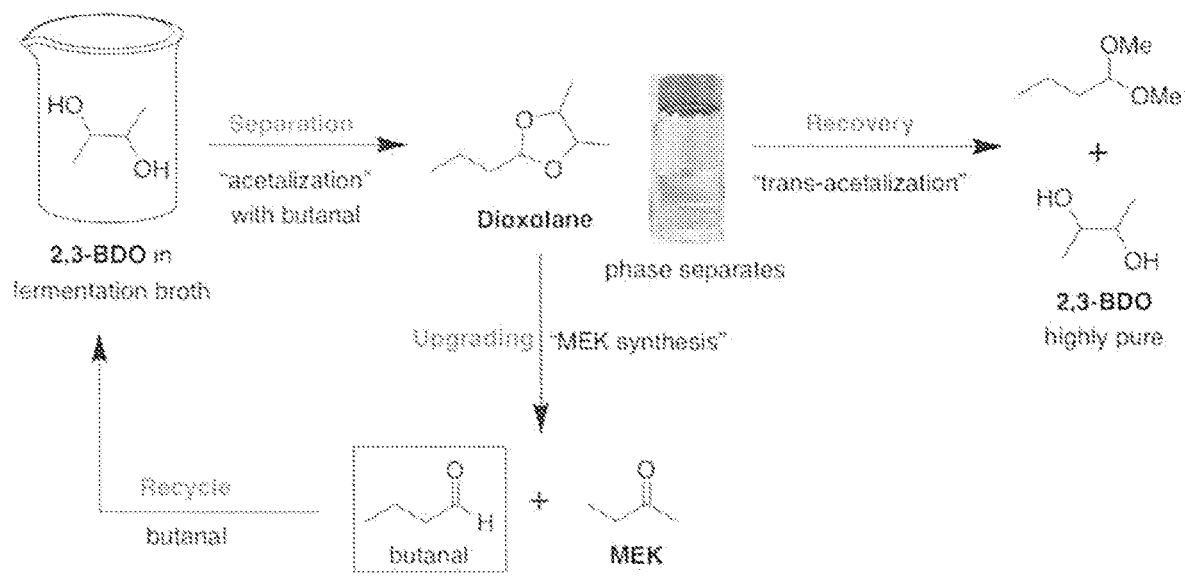
FIG. 1A Graphical abstract of the process.
Figure 1A:
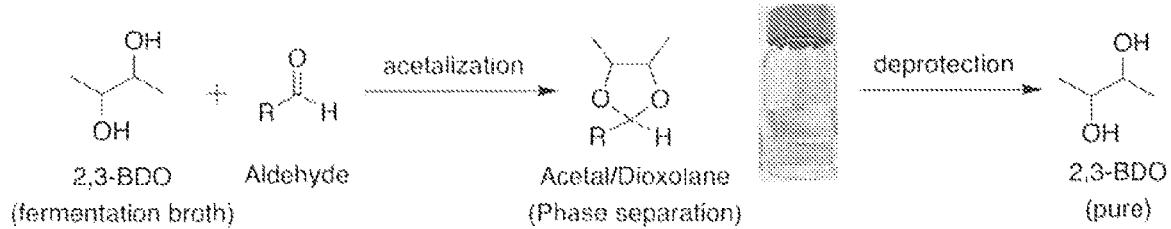

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized.

The present invention is directed to a method for the separation, recovery and upgrading of biomass derived 2, 3-butanediol (2,3-BDO). The invention is directed to a method for separation and recovery of 2,3-butanediol (2,3-BDO) from fermentation broth, said process comprising the steps of:
  a) Acetalization of fermentation broth with an aldehyde in the presence of a heterogeneous catalyst forming cyclic acetal (dioxolane);
  b) Isolating 2,3-BDO as phase-separated dioxolane;
  c) Transacetalization of phase-separated dioxolane with methanol followed by distillation of acetal, to obtain high purity 2,3-BDO and butyraldehyde dimethyl acetal;
  d) Distilling off butyraldehyde dimethyl acetal; and
  e) Recovering high purity 2,3-BDO.

Another embodiment of the present invention is directed to the conversion of dioxolane as a 2,3-BDO synthon to synthetically important dehydration product methyl ethyl ketone (MEK). The cyclic acetal (dioxolane) produced from the reaction between butyraldehyde and BDO to demonstrate butyraldehyde recyclability. The method comprising cleavage of dioxolane with an acid catalyst to obtain MEK and butyraldehyde. Recycling by adding the recovered butanal with MEK and butanal to the fermentation broth.

In a first embodiment, the catalyst employed in the method comprises acetic acid, aluminum oxide, aluminum phosphate, ZSM-5 with silicon/aluminum:80, Nafion NR50® and Amberlyst-15®. More preferably, ZSM-5; most preferably, Nafion NR50® and Amberlyst-15®.

In a particular embodiment, the catalyst employed comprises aluminum oxide, aluminum phosphate, and ZSM-5 with silicon/aluminum. The amount of catalyst employed is about 50% to about 60% by weight. The temperature is conducted at about 290° C. to about 325° C. A preferred catalyst is aluminum oxide; more preferably, aluminum phosphate; most preferably, ZSM-5.

In another embodiment, the catalyst is selected from Nafion NR50® and Amberlyst-15®. The amount of catalyst employed is preferably about 10% by weight, more preferably, about 20% by weight and most preferably, about 30% by weight. Optimizations were conducted to study the effect of different catalysts, reaction temperature, solvents and equivalents of selected aldehyde on the formation of dioxolane. The temperature is conducted at room temperature and about 40° C. The solvent employed in the method of the present invention is selected from tetrahydrofuran (THF), THF/water, THF/water (3:1) and methyl-THF/water (3:1). The most preferred solvent is THF.

Another embodiment of invention is the aldehyde employed in the present invention comprises butanal, hexanal, octanal, 2-ethylbutanal and 2-ethyl hexanal. Initial screening was conducted to select the aldehyde that reacts efficiently to form phase separated dioxolanes. The most preferred aldehyde is butanal.

Another embodiment of the invention is directed to 2,3-BDO separation experiments conducted with three types of aqueous solutions. The aqueous solutions are selected from aqueous butanediol (BDO), BDO broth mimic fermentation broth and actual fermentation broth.

Another embodiment of the invention is directed to the unexpected high purity of the method according to the present invention. It provides isolation yield of high purity 2,3-BDO of about 90%.

Another embodiment of the invention relates to the recycling and reuse of the catalyst. The recovered catalyst is still reactive after about ten cycles.

As used herein, Nafion NR50® Polymerbeads are perfluorosulfonic acids (PFSA) superacid resin is a bead-form, strongly acidic resin developed for heterogeneous acid catalysis of a wide variety of organic reactions. It is a copolymer of tetrafluoroethylene and perfluoro-3,6-dioxa-4-methyl-7-octenesulfonyl fluoride. Nafion NR50® is available from Dupont. Amberlyst-15® is available from Sigma Aldrich or Dupont. It is a macro reticular polystyrene based ion exchange resin with strongly acidic sulfonic group. It serves as an excellent source of strong acid. It can also be used several times. Amberlyst 15® is a heat sensitive macro-porous sulfonic ion exchange acid resin which could be used as a catalyst.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The process of the present invention is illustrated further below by reference to examples which are intended to be illustrative and are not construed to limit the present invention in any way.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All the chemicals and solvents used in this study were purchased from commercial sources and used as received unless otherwise specified. 2,3-Butanediol (2,3-BDO) and aldehydes (butyraldehyde, 2-ethylbutyraldehyde, hexanaldehyde, 2-ethylhexandaldehyde and octanal) were purchased from Sigma-Aldrich. Aluminum oxide ($Al_2O_3$) and aluminum phosphate ($AlPO_4$) purchased from Sigma-Aldrich, and ZSM-5 with Si/Al: 80 purchased from Zeolyst. 2,3-BDO fermentation broths were obtained from National Renewable Energy Laboratory, NREL (Colorado, USA). Two types of fermentation broths were: pure sugar (2,3-BDO conc. 59.7 g/L) and hydrolysate (2,3-BDO conc. 79.1 g/L). 1H NMR spectra for quantitative analysis were collected at room temperature on a Bruker AV400 MHz spectrometer. Chemical shifts were referenced to the residual solvent signal. Agilent 7890 GC system equipped with an Agilent 5975 mass selective detector (MSD), a flame ionization detector (FID), and a PolyArc system was used for GC-MS analysis.

BDO Separation Experiments 2,3-BDO separation experiments were carried out with three types of aqueous solutions; aqueous BDO (70 g/L), BDO broth mimic and actual fermentation broths (both pure sugar and hydrolysate broths).

Dioxolane Synthesis—Reaction Condition Optimization

All the optimization experiments were performed on a small scale (1 mL aqueous BDO solution), and analysis performed using GS-MS. As part of reaction conditions optimization, acetalization of aqueous BDO (70 g/L) was conducted with five different bio-derived aldehydes. This initial screening was conducted to select the aldehyde that reacts efficiently to form phase-separated dioxolanes. Furthermore, optimizations were carried out to study effect of different catalysts, reaction temperature and equivalents of selected aldehyde on the formation of dioxolane. Later, catalyst recycling experiments were also performed to analyze efficiency of the catalyst under optimized conditions with the aqueous BDO solution.

Isolated Yield Calculations

Experiments to calculate isolated yield of the phase separated dioxolane formed were conducted on a larger scale (50 mL), and results were reported based on quantitative NMR analysis (SI). Integration ratio of C2-methylene proton of butyraldehyde (excess) and C2-methylene of dioxolane formed were used for the isolated yield calculations.

BDO Recovery Experiments

Trans-acetalization (methanolysis) experiments were conducted on the dioxolane samples that were obtained from the separation experiments. Analytically pure 2,3-BDO was recovered by distilling-off butyraldehyde dimethyl acetal formed in the reaction.

Conversion of Dioxolane to Methyl Ethyl Ketone and Butyraldehyde Recovery

Cleavage of the acetal (dioxolane) over acid catalyst(s) was conducted in a plug flow reactor at atmospheric pressure and at 1 $h^{-1}$ weight hourly space velocity (WHSV) over three different solid acid catalysts. The catalyst testing was conducted on a down flow reactor arrangement. The catalyst of interest was placed in the middle of the reactor tube in an isothermal zone and heated using a band heater to the desired reaction temperature. Dioxolane (using a HPLC pump) and carrier gas nitrogen ($N_2$) were fed from the top of the reactor. The liquid product samples were collected at the bottom of the reactor in a cold trap. The products were speciated via gas chromatography-mass spectroscopy (GC-MS) and quantified with a flame-ionization detector (FID) using internal/external standards. The non-condensable gases from the cold trap passed through a flow meter (DryCal) and their composition was analyzed in a gas chromatography-thermal conductivity detector (GC-TCD). The results reported were from the samples collected after time on stream of 24 hour.

Dioxolane conversion and product carbon yield were calculated by the following equations:

$$\text{Dioxolane conversion (\%)} = \frac{\text{mole of dioxolane consumed}}{\text{mole of dioxolane fed}} \times 100$$

$$\text{Product carbon yield (\%)} = \frac{\text{carbon mole of product produced}}{\text{carbon mole of dioxolane fed}} \times 100$$

Results and Discussion

Our strategy for the first approach involves BDO separation from broth using acetalization, and then recovery of BDO from the phase-separated dioxolanes (Scheme 1, FIG. 1B).

BDO Separation (Acetalization Approach)

A range of aldehydes that can facilitate the phase separation step upon dioxolane formation was initially screened. As part of reaction conditions optimization, acetalization of aqueous solution of BDO (70 g/L) with five different bio-derived aldehydes was first carried out. Following our recent work, we first compared reactivity of these aldehydes to form phase-separated dioxolane with Amberlyst-15® as catalyst, both at room temperature and 40° C. Dioxolane formation worked with varying degree of efficiency in these cases using Amberlyst-15® (Table 1). Based on results, we identified butyraldehyde as a viable candidate for further process optimization.

TABLE 1

Efficiency (% conversion) of acetalization with 2,3-BDO$^a$.

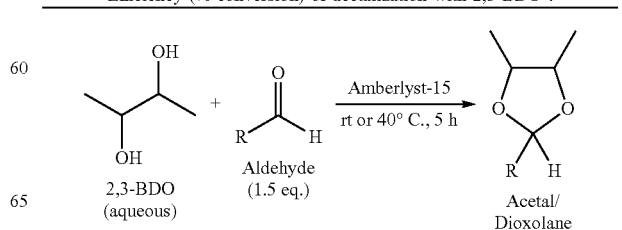

TABLE 1-continued

| Aldehyde | % dioxolane[b] | |
|---|---|---|
| | at room temp. | at 40° C. |
| Butanal | 74 | 80 |
| Hexanal | 69 | 75 |
| Octanal | 20 | 31 |
| 2-Ethylbutanal | 25 | 34 |
| 2-Ethylhexanal | 5 | 9 |

[a]Reaction condition: Aq. BDO (1 mL of 70 g/L solution); aldehyde (1.5 eq); Amberlyst-15 (10 wt.%);
[b]based of GC analysis We next focused on to further optimize reaction conditions for the separation of BDO from aqueous solution. Reactive extraction (acetalization) approach was followed where BDO and butyraldehyde reacts to form phase separated dioxolanes (Scheme 2).

Scheme 2. BDO separation using reactive-extraction (acetalization) approach.

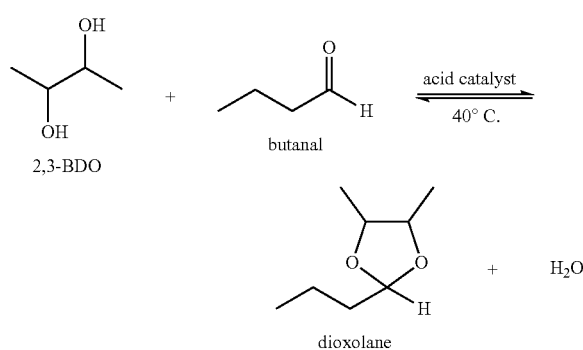

Optimization studies were performed using aqueous BDO solution (containing 70 g/L BDO). Catalyst (acetic acid, Amberlyst-15® and Nafion NR50®) screening and effect of temperature and equivalents of butyraldehyde was studied. Results from these studies are summarized below.

Optimization of Reaction Conditions

We initially attempted acetalization (with 1.5 eq butyraldehyde and 40° C.) using no catalyst and by using amount of acetic acid that is typically found in the broth composition. These reactions resulted in nearly about 10-15% conversion of BDO to dioxolane (based on GC analysis). Nearly 60% conversion was observed when amount of acetic acid was increased to 100 μL. Generally, as a process, the use of heterogeneous solid acid catalyst is advantageous and industrially applicable.

Reactions performed in heterogeneous conditions are more amenable to product isolation with recycling and reuse of catalyst. The use of heterogeneous solid acid-catalyst, Amberlyst-15® (about 10 wt. %), resulted in about 80-82% conversion of BDO to dioxolane as confirmed by GC analysis. However, increasing catalyst loading beyond 10 wt. % did not improve conversion. The reactivity of another heterogenous acid catalyst (Nafion NR 50®) to Amberlyst-15® for the acetalization reaction was compared. Both Nafion NR 50® and Amberlyst-15® showed similar reactivities in conversion of BDO to dioxolane in about 3 hrs., suggesting either of these could be employed in the separation process. Amberlyst-15® is inexpensive and widely applicable, and Nafion NR50® catalyst as beads are easy to separate.

We then studied effect of increasing equivalents of butyraldehyde under heterogeneous catalyst system (about 10 wt % Amberlyst-15®). Complete conversion was observed when butyraldehyde concentration was increased to 5 equivalents in 3 hr. reaction time. However, increasing reaction temperature has no positive effect on the conversion rate of reaction (with 5 eq of butyraldehyde). The % conversion dropped when temperature was increased to about 55° C. This might be due to the shift in the equilibrium of the dioxolane formation.

With optimized conditions in hand, the catalyst recycling of Nafion NR50® beads was tested, exclusively chosen for the small scale (1.6 mL aqueous BDO solution) experiment mainly for the ease of handling. However, as pointed, Amberlyst-15® is equally reactive. There was no change in the catalytic activity of Nafion NR50® beads even after about 10 cycles. Filtration was used to recover the catalyst.

Heterogeneous Solid-Acid Catalyzed BDO Separation

Figure 2:
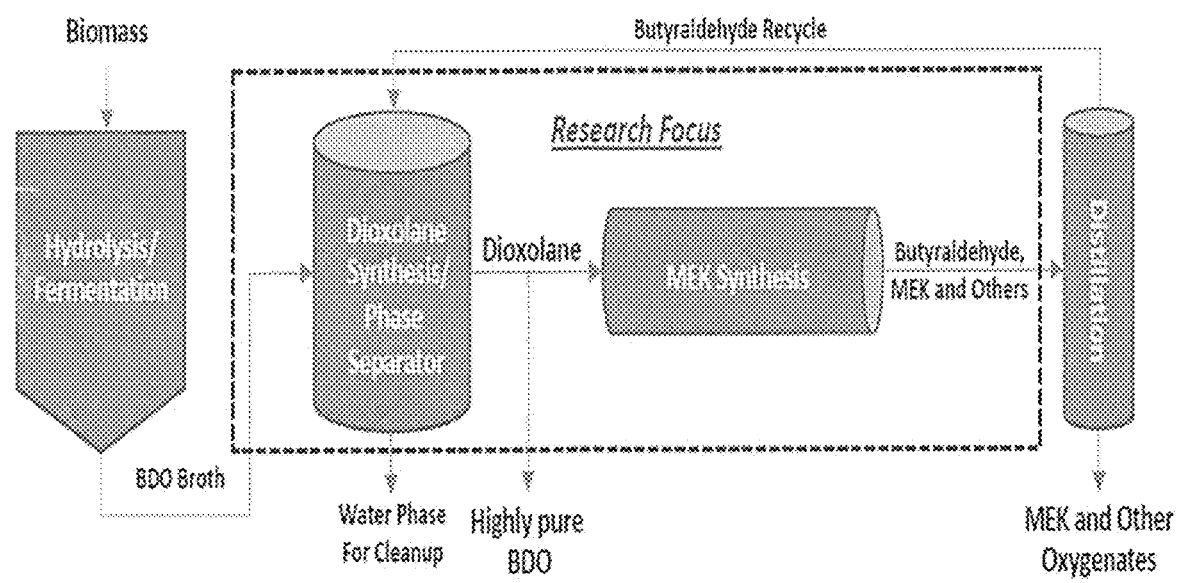
FIG. 2. Simplified integrated process flow diagram for BDO separation and conversion to methyl ethyl ketone (MEK) from biomass. Separation and recovery of BDO from biomass as phase separated dioxolane and conversion of dioxolane to MEK.

After optimizing reaction conditions, we then tested these conditions on a larger scale in order to determine isolated yields for phase separated dioxolane formation. BDO separation experiment were carried out using 50 mL aqueous BDO solution using optimized conditions (5 eq butyraldehyde and about 10 wt. % Nafion NR50® at 40° C. for 5 hr.). Dioxolane phase separation Was observed upon reaction completion and no detectable BDO was observed in the aqueous layer. Phase separated layer was isolated and analyzed by NMR. Based on NMR analysis, nearly about 82% of dioxolane was formed in the reaction (FIG. 2).

Based on the results from experiments with aqueous BDO solution, we next attempted separation of BDO from broth mimic. Table 2 summarizes composition of two different 2,3-butanediol (2,3-BDO) fermentation broths received from NREL. Broth mimic of pure sugar broth was prepared based on composition as outlined in Table 2.

TABLE 2

Composition of 2,3-BDO fermentation broth.

| Compound | Pure Sugar broth (g/L) | Hydrolysate broth (g/L) |
|---|---|---|
| 2,3-BDO | 59.7 | 79.1 |
| Glucose | 0.3 | 1.4 |
| Xylose | 8.0 | 2.0 |
| Arabinose | 0.7 | 6.0 |
| Acetoin | 8.3 | 3.3 |
| Glycerol | 3.0 | 5.1 |
| Xylitol | 2.5 | 1.0 |
| Lactic acid | 1.3 | 2.0 |
| Ethanol | 0.5 | 0.8 |
| Acetic acid | 0.8 | 1.5 |

Figure 3:
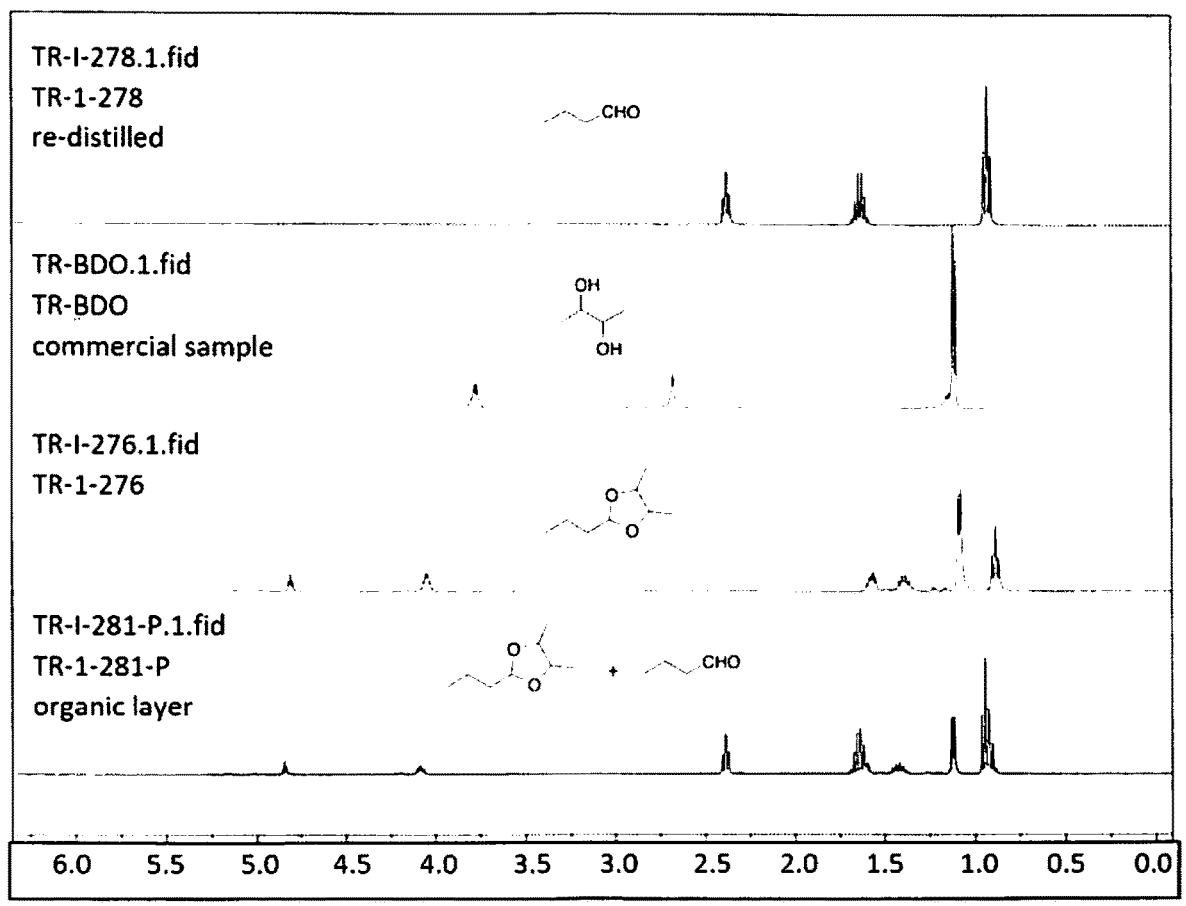
FIG. 3. Graph showing the NMR analysis of BDO separation (dioxolane formation from aqueous BDO) experiment.

We first individually assessed reactivity of other broth components (mainly glucose, xylose, xylitol, arabinose, glycerol) with butyraldehyde under optimized conditions. These experiments were performed in order to identify acetal as contaminant (if any) that is derived from components other than BDO in the product mixture. To our expectation, no dioxolane formation was observed for these components except for glycerol; the product of which was hydrophilic enough to not phase separate. Similar to aqueous BDO solution experiment, reaction with BDO troth mimic also resulted in phase separation of dioxolane. NMR analysis of the phase separated layer (contains dioxolane plus unreacted butyraldehyde) showed 82% yield for the dioxolane formed with no detectable byproducts/contaminants (FIG. 3). The BDO in the broth mimic got phase separated as organic dioxolane product from the reaction and all other polar sugar components remained in the aqueous layer.

Figure 4:
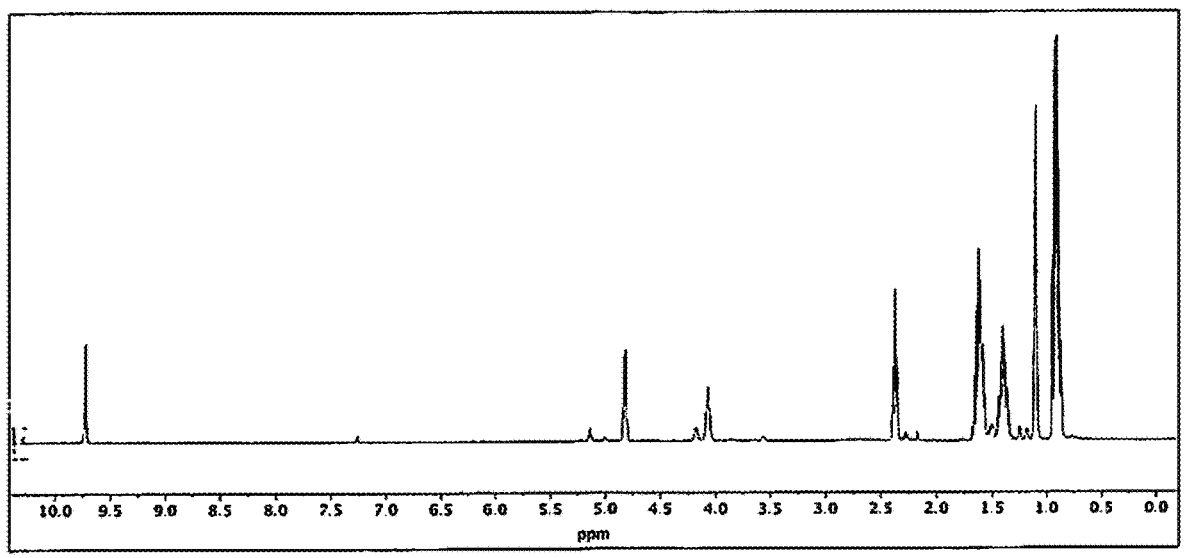
FIG. 4 Graph showing the NMR of the isolated organic layer from BDO broth mimic reaction. Mixture of product dioxolane and butyraldehyde (excess) obtained as a phase separated layer upon reaction.

Encouraged by these results, we then tested this process (acetalization approach) in BDO isolation from the actual broth. Acetalization was carried out with 20 mL of pure sugar broth (BDO concentration 59.7 g/L) using 5 equivalent butyraldehyde and about 10 wt. % Nafion NR50® catalyst at about 40° C. for about 5 hr. After 5 hr., the top layer was separated and analyzed by NMR. Surprisingly very low conversion of BDO to dioxolane (~10%) was observed in reaction with actual broth (FIG. 4a). This could be due to very complex nature of the actual broth that affects catalyst activity. Similar results were obtained when reaction was carried out with hydrolysate broth (BDO concentration 79.1 g/L). However, Amberlyst-15® showed drastic increase in reactivity with pure sugar broth, complete conversion and nearly about 82% isolated yield for dioxolane (FIG. 4b). Additionally, the economical catalyst (Amberlyst-15®) showed similar efficiency in isolating aqueously dissolved BDO from hydrolysate broth into phase separated dioxolane.

Recovery of BDO from the Phase-Separated Dioxolane (Trans-Acetalization)

After successfully isolating BDO from aqueous medium in the form of phase separated dioxolanes, our focus was to optimize reaction conditions to recover pure BDO from dioxolanes. The dioxolanes formed upon acetalization of can be deprotected chemically to generate BDO in pure form (Scheme 3).

Scheme 3. Deprotection of dioxolane to generate 2,3-BDO.

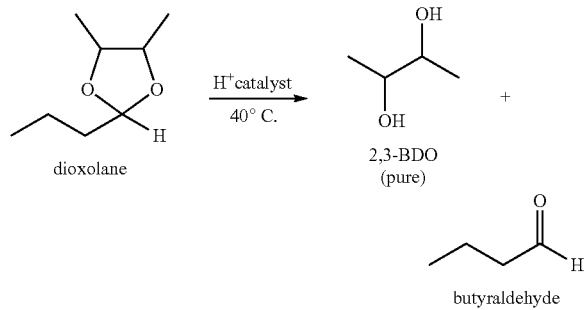

Hydrolysis or deprotection of acetal is a well-known reaction. There are several reports of using heterogenous catalyst for these reactions, mainly as an advantageous process for the ease of recycling catalyst during work-up. Several reaction conditions were attempted for complete recovery of BDO. Preliminary results from the deprotection experiments looked promising. These results are summarized in Table 3.

Among solid acid catalysts, Nafion NR50® has shown to be an effective catalyst for wide range of reactions. Using Nafion NR50® (about 30 wt. %) as catalyst in aqueous THF resulted in nearly about 70% conversion to BDO in the deprotection reaction of dioxolane. On a small scale (100 mg dioxolane) using Nafion NR50® (about 30 wt. %) as catalyst in aqueous THE resulted in nearly about 70% conversion to BDO in the deprotection reaction of dioxolane. And since the reaction is equilibrium controlled, isolating butyraldehyde drives the reaction to completion. However, reaction showed moderate results (35% conversion with about 25% BDO formed) on a larger scale. This is due to loss of THE while isolating butanal from the reaction mixture, thus making the solution immiscible. Reaction was too slow with drop in percent conversion (32% conversion) was observed if 1:1 $H_2O$:THF was used as solvent. Dioxane showed better solubility with water in presence of dioxolane, however reaction was too slow with formation of side products (40% conversion after about 48 h with 18-20% un-identified side-products).

TABLE 3

BDO recovery (deprotection of acetal) experiments[a]

| Catalyst | Catalyst Loading (wt.%) | Solvent | Time (hrs.) | % Conversion[b] |
|---|---|---|---|---|
| La (OTf)$_3$ | 30 | THF/Water (3:1) | 3 | No reaction |
|  |  |  | 24 | 9.6% BDO |
| Nafion NR50 ® | 30 | No solvent | 3 | No reaction |
|  |  |  | 24 | n.d. |
| Nafion NR50 ® | 30 | THF/Water (3:1) | 3 | No reaction |
|  |  |  | 24 | 68.9% BDO |
| No catalyst | — | THF/Water (3:1) | 3 | No reaction |
|  |  |  | 24 | 8.3% BDO |
| Nafion NR50 ® | 20 | Me—THF/Water (3:1) | 15 | No reaction |
| Nafion NR50 ® | 20 | GVL/Water (3:1) | 15 | No reaction |
| Amberlsyt-36 | 20 | THF/Water (1:1) | 24 | 32% conversion |

[a]Reaction condition: 100 mg dioxolane, catalyst (0-30 wt.%) in specified solvent at 40° C.;

Reactions were also conducted under reduced pressure (500 mbar and 700 mbar) to push the equilibrium. However, these attempts were unsuccessful as the dioxolane distills off on rotary evaporator under these pressure condition. As green solvent alternatives, Me-THF and GVL were tried for this reaction. Due to immiscible nature of these solvents, no conversion was observed in reaction.

[b]Based on GC-MS analysis

Methanolysis (trans-acetalization) is an alternative way to recover BDO (Scheme 4). Dioxolane upon treatment with methanol in presence of solid acid catalyst is converted to dimethyl acetal of butyraldehyde and BDO.

Scheme 4. Trans-acetalization of dioxolane with methanol.

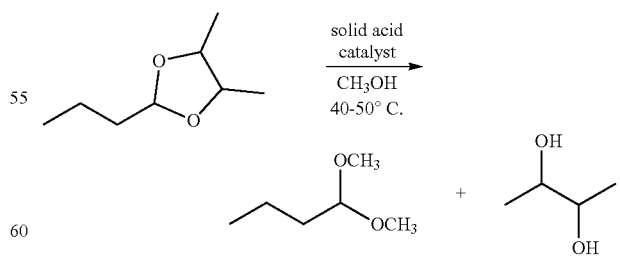

Figure 5:
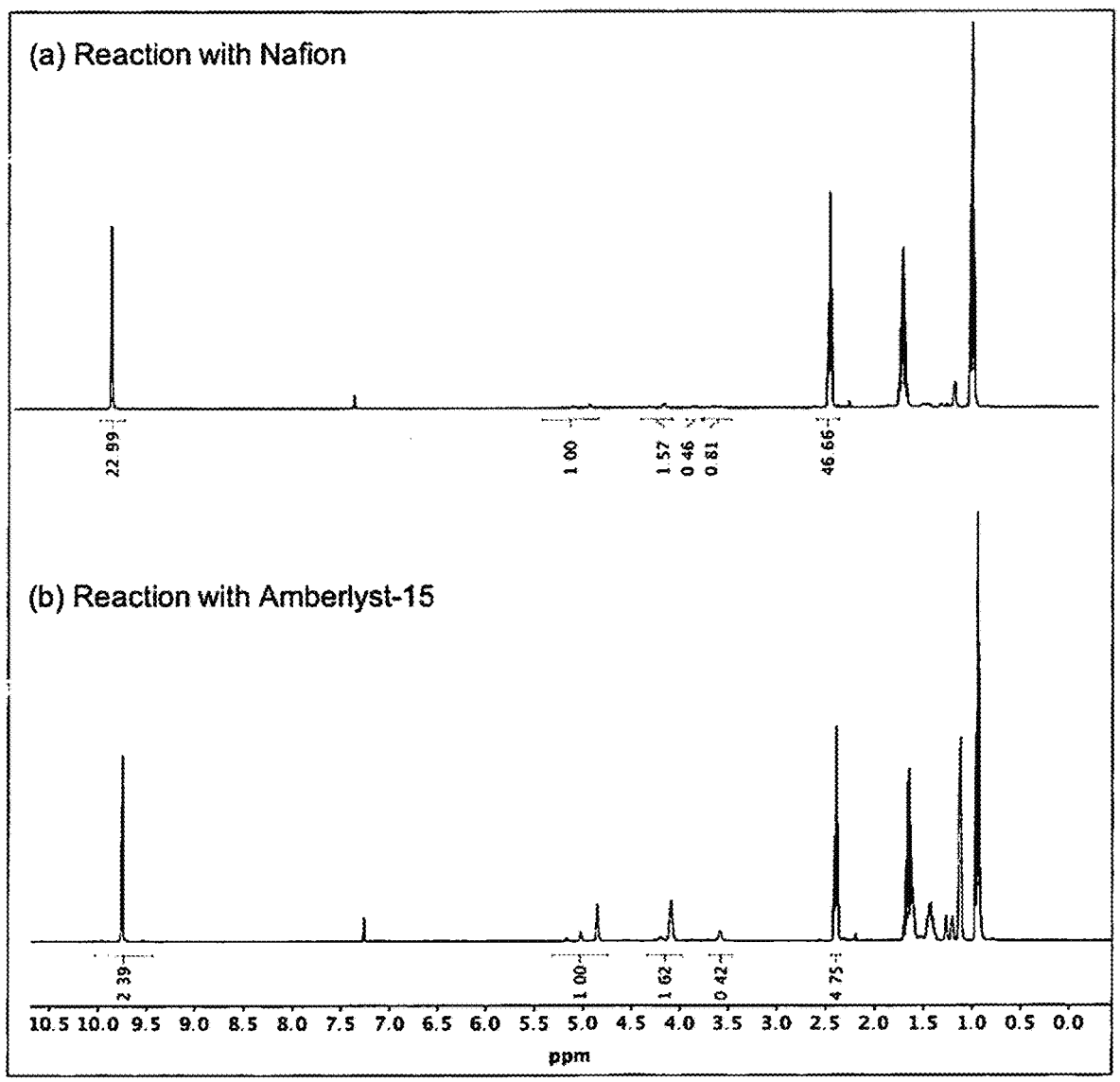
FIG. 5 Graph showing NMR for isolated organic layer (contains dioxolane formed and excess butyraldehyde) after reaction with a) Nafion NR50® and b) Amberlyst 15® as a catalyst. Percent yield of dioxolane formed calculated based on NMR integrations.
Figure 6:
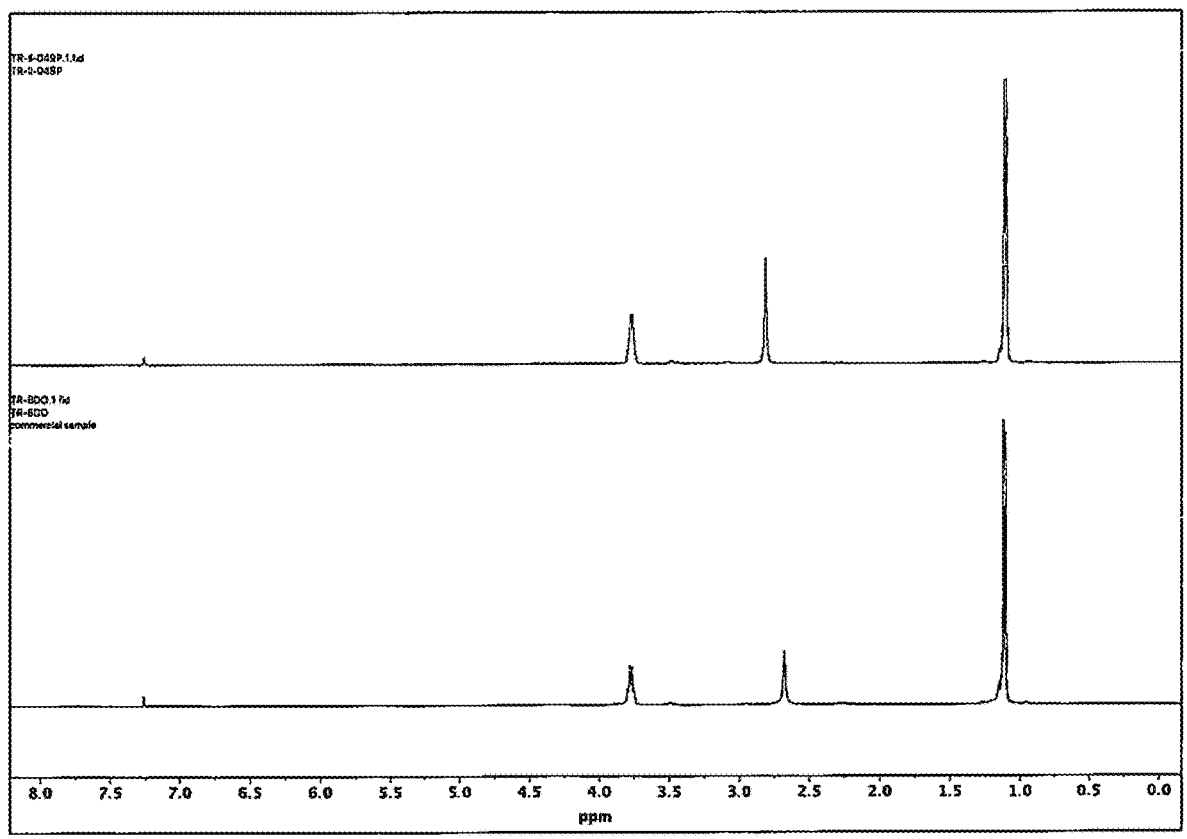
FIG. 6 Graph showing NMR comparison of isolated BDO (top) with commercial sample (bottom)

On a small scale (200 mg) nearly about 90-95% conversion and about 70% isolated yield of BDO was obtained in methanolysis using Nafion NR50® (20 wt. %). Amberlyst-15® as catalyst yielded similar results. A very high purity BDO (>99%, based on NMR and GC) with an isolated yield of nearly about 75% was obtained when the reaction was carried out on a gram scale. A drastic increase in isolated yield (nearly about 90%) was observed when methanolysis was carried out on 10 g scale. NMR comparison of the isolated BDO with that of commercial sample is shown in FIG. 5.

Upgrading BDO (Conversion to MEK and Butyraldehyde Recovery)

Our second approach for the integrated process involves conversion of biomass to MEK via the dioxolane intermediate. The main objective of this approach is to maximize the butyraldehyde recycle by avoiding its participation in the condensation reaction and simultaneously generate the MEK and its derivatives for the fuels generation. The cleavage of dioxolane was studied over an acid catalyst to identify the viability of this approach. The reaction scheme for the dioxolane cleavage is shown in Scheme 5.

Scheme 5. Reaction scheme showing the dioxolane conversion over acid catalyst.

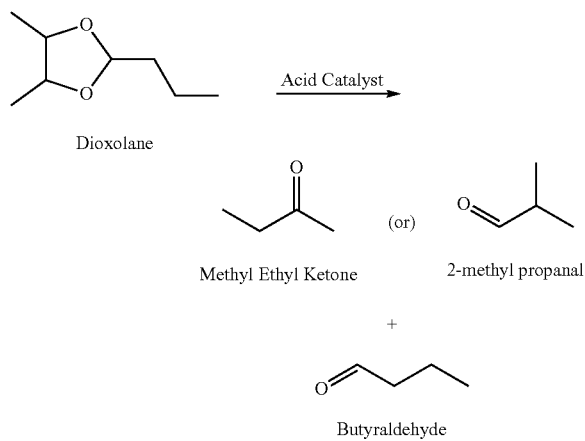

Cleavage of the acetal over acid catalyst(s) was conducted in a plug flow reactor at atmospheric pressure and at 1 h$^{-1}$ weight hourly space velocity (WHSV) over three different solid acid catalysts. The results from the experimental work is listed in the Table 4. The catalysts tested for this initial study were 1) aluminum oxide ($Al_2O_3$), 2) aluminum phosphate ($AlPO_4$) and 3) ZSM-5 with Si/Al: 80 were tested at 290° C. and 325° C. temperature.

Conversion of dioxolane was different for all three catalyst at 290° C. (ZSM-5>$AlPO_4$>$Al_2O_3$) but for the temperature at 325° C., all three catalysts performed at conversion levels >95%. Among the catalysts tested ZSM-5 shows the best selectivity to butyraldehyde (close to the stoichiometric value around 50%) and $AlPO_4$ has the lowest selectivity to butyraldehyde. The lower selectivity of butyraldehyde is due to the promotion of self-aldol condensation of butyraldehyde and the cross-aldol condensation between the butyraldehyde and MEK (or 2-methyl propanal).

TABLE 4

Dioxolane conversion to butyraldehyde and methyl ethyl ketone at various solid acid catalyst. Atmospheric pressure, 1 h$^{-1}$ weight hourly space velocity.

| Catalyst | Reaction Temp. (° C.) | Dioxolane Conv (%) | Product Carbon Yield (%) | | | | | |
|---|---|---|---|---|---|---|---|---|
| | | | Butyl | MEK | 2-MP | C4+ Ketone | C4+ Aldehyde | Other |
| $Al_2O_3$ | 290 | 82.0 | 27.4 | 16.6 | 2.6 | 0.6 | 0.4 | 52.4 |
| $Al_2O_3$ | 325 | 98.6 | 43.0 | 25.8 | 5.2 | 1.3 | 1.3 | 23.4 |
| $AlPO_4$ | 290 | 98.4 | 35.4 | 27.6 | 6.9 | 3.5 | 2.2 | 24.3 |
| $AlPO_4$ | 325 | 99.5 | 39.8 | 26.9 | 8.8 | 4.1 | 2.2 | 18.1 |
| ZSM-5 (Si/Al:80) | 290 | 100.0 | 46.6 | 23.5 | 12.8 | 1.0 | 0.0 | 16.2 |
| ZSM-5 (Si/Al:80) | 325 | 100.0 | 50.0 | 24.9 | 13.8 | 1.0 | 0.0 | 10.3 |
| ZSM-5 (Si/Al:280) | 290 | 98.5 | 44.8 | 25.2 | 12.7 | 1.0 | 0.0 | 16.2 |
| ZSM-5 (Si/Al:280) | 325 | 99.7 | 40.7 | 22.6 | 13.1 | 2.4 | 0.0 | 21.2 |

Butyl: Butyraldehyde,
MEK: Methyl ethyl ketone,
2-MP: 2-Methyl propanal

Both MEK and its isomer 2-methyl propanal was generated by all three acid catalysts and the ZSM-5 showed the highest selectivity to the 2-methyl propanal. The combined selectivities between the MEK and 2-methyl propanal for all the catalyst is about 40% (stoichiometric level is about 50%). Lower selectivity of MEK (plus 2-methyl propanal) is due to the formation of C8+ compound formation from the condensation reaction. The condensation products can be sent to the fuel synthesis step along with MEK so overall carbon efficiency to the BDO to fuels should be close to stoichiometric levels from this approach.

CONCLUSIONS

While several biochemical approaches have been developed for 2,3-BDO production in high concentrations, there still exists the challenges to isolate and recover highly pure BDO in an efficient manner. We have demonstrated a complete separation, recovery and upgrading process for 2,3-BDO from biomass using an efficient and suitable heterogeneous catalyst system. The integrated process is a systematic two-way approach that allows for recovery of BDO in highly pure form and upgrading to highly useful synthetic precursor, methyl ethyl ketone (MEK). Reactive extraction (acetalization) approach was followed where BDO and n-butyraldehyde reacts to form phase separated dioxolanes. Under optimized conditions, using either Nafion NR50® or Amberlyst-15® as catalyst, we observed complete conversion of BDO to form dioxolane in about hrs. Complete conversion (based on GC analysis) and nearly about 80-90% isolated yield of high purity dioxolane was obtained upon reactive extraction of BDO from aqueous solutions including fermentation broths. A very high purity BDO (>99%, based on NMR and GC) with an isolated yield of nearly about 90% was obtained upon methanolysis of the phase separated dioxolane. Also, the dioxolane cleavage was successfully demonstrated with ~stoichiometric equivalent selectivity to butyraldehyde and MEK plus derivatives. The in situ generation of MEK (plus its derivatives) in the dioxolane cleavage step reduces the number of unit operation required to produce fuels from the BDO broth. Additionally, the use of heterogeneous catalysts holds the promise for future development of an economical and environmentally friendly downstream process for 2,3-BDO.

REFERENCES

The following references, as well as other references cited in the present application, to the extent that they provide exemplary procedural or other details supplementary to those set forth herein, are specifically incorporated herein by reference.

1. H. Gräfje, Körnig, W., Weitz, H.-M., Reiß, W., Steffan, G., Diehl, H., Bosche, H., Schneider, K. and Kieczka, H., in Ullmann's Encyclopedia of Industrial Chemistry, 2000, DOI: 10.1002/14356007.a04_455, pp. 1-12.
2. Y. Zhang, D. Liu and Z. Chen, Biotechnology for Biofuels, 2017, 10, 299.
3. O. Hakizimana, E. Matabaro and B. H. Lee, Biotechnology Reports, 2020, 25, e00397.
4. Y.-G. Lee and J.-H. Seo, Biotechnology for Biofuels, 2019, 12, 204.
5. E. Celińska and W. Grajek, Biotechnology Advances, 2009, 27, 715-725.
6. W. Zhang, D. Yu, X. Ji and H. Huang, Green Chemistry, 2012, 14, 3441-3450.
7. H. Duan, Y. Yamada and S. Sato, Applied Catalysis A: General, 2015, 491, 163-169.
8. A. M. Bialkowska, World Journal of Microbiology and Biotechnology, 2016, 32, 200.
9. Q. Zheng, M. D. Wales, M. G. Heidlage, M. Rezac, H. Wang, S. H. Bossmann and K. L. Hohn, Journal of Catalysis, 2015, 330, 222-237.
10. B. G. Harvey, W. W. Merriman and R. L. Quintana, ChemSusChem, 2016, 9, 1814-1819.
11. K. W. Harrison and B. G. Harvey, Sustainable Energy & Fuels, 2018, 2, 367-371.
12. GLOBAL 2,3 BUTANEDIOL MARKET RESEARCH REPORT 2020, 2020.
13. Global 2,3 Butanediol Market Insights, Forecast to 2025, 2019.
14. X.-J. Ji, H. Huang and P.-K. Ouyang, Biotechnology Advances, 2011, 29, 351-364.
15. D.-K. Kim, C. Rathnasingh, H. Song, H. J. Lee, D. Seung and Y. K. Chang, Journal of Bioscience and Bioengineering, 2013, 116, 186-192.
16. R. Yamada, R. Nishikawa, K. Wakita and H. Ogino, Journal of Industrial Microbiology & Biotechnology, 2018, 45, 305-311.
17. Z. Yang and Z. Zhang, Biotechnology for Biofuels, 2018, 11, 35.
18. L.-q. Jiang, Z. Fang, X.-K. Li and J. Luo, AMB Express, 2013, 3, 48.
19. S. Cho, T. Kim, H. M. Woo, Y. Kim, J. Lee and Y. Um, Biotechnology for Biofuels, 2015, 8, 146.
20. S. K. Garg and A. Jain, Bioresource Technology, 1995, 51, 103-109.
21. S. Yang, A. Mohagheghi, M. A. Franden, Y.-C. Chou, X. Chen, N. Dowe, M. E. Himmel and M. Zhang, Biotechnology for Biofuels, 2016, 9, 189.
22. United States Pat., 2019.
23. N. Qureshi, M. M. Meagher and R. W. Hutkins, Separation Science and Technology, 1994, 29, 1733-1748.
24. S. Jeon, D.-K. Kim, H. Song, H. J. Lee, S. Park, D. Seung and Y. K. Chang, Journal of Bioscience and Bioengineering, 2014, 117, 464-470.
25. S. D. Birajdar, S. Rajagopalan, J. S. Sawant and S. Padmanabhan, Process Biochemistry, 2015, 50, 1449-1458.
26. C. J. Davey, A. Havill, D. Leak and D. A. Patterson, Journal of Membrane Science, 2016, 518, 150-158.
27. P. Shao and A. Kumar, Journal of Membrane Science, 2009, 329, 160-168.
28. P. Shao and A. Kumar, The Canadian Journal of Chemical Engineering, 2011, 89, 1255-1265.
29. P. Drabo, T. Tiso, B. Heyman, E. Sarikaya, P. Gaspar, J. Förster, J. Büchs, L. M. Blank and L. Delidovich, ChemSusChem, 2017, 10, 3252-3259.
30. J.-Y. Dai, C.-J. Liu and Z.-L. Xiu, Process Biochemistry, 2015, 50, 1951-1957.
31. G. Li, W. Liu, X. Wang and Q. Yuan, Chemistry Letters, 2013, 43, 411-413.
32. J. Haider, G. R. Harvianto, M. A. Qyyum and M. Lee, ACS Sustainable Chemistry & Engineering, 2018, 6, 14901-14910.
33. G. R. Harvianto, J. Haider, J. Hong, N. Van Duc Long, J.-J. Shim, M. H. Cho, W. K. Kim and M. Lee, Biotechnology for Biofuels, 2018, 11, 18.
34. J. Haider, M. A. Qyyum, L. Q. Minh and M. Lee, Chemical Engineering Research and Design, 2020, 153, 697-708.
35. Z.-L. Xiu and A.-P. Zeng, Applied Microbiology and Biotechnology, 2008, 78, 917-926.
36. Y. Li, Y. Wu, J. Zhu, J. Liu and Y. Shen, Journal of Saudi Chemical Society, 2016, 20, S495-S502.
37. Y. Li, Y. Wu, J. Zhu and J. Liu, Biotechnology and Bioprocess Engineering, 2012, 17, 337-345.
38. O. Staples, Cameron M. Moore, J. H. Leal, T. A. Semelsberger, C. S. McEnally, L. D. Pfefferle and A. D. Sutton, Sustainable Energy & Fuels, 2018, 2, 2742-2746.
39. E. H. Cordes and H. G. Bull, Chemical Reviews, 1974, 74, 581-603.
40. S. L. Repetto, J. F. Costello, C. P. Butts, J. K. W. Lam and N. M. Ratcliffe, Beilstein Journal of Organic Chemistry, 2016, 12, 1467-1475.
41. M. A. Harmer, 2002, DOI: doi:10.1002/9780470988305.ch6, 86-119.
42. T.-S. Li and S.-H. Li, Synthetic Communications, 1997, 27, 2299-2303.
43. K. Tomonori, K. Masaki, M. Tomoo, E. Kohki and K. Kiyotomi, Chemistry Letters, 2003, 32, 648-649.
44. G. M. Coppola, Synthesis, 1984, 1984, 1021-1023.
45. M. A. Harmer and Q. Sun, Applied Catalysis A: General, 2001, 221, 45-62.
46. M. A. Harmer, W. E. Farneth and Q. Sun, Journal of the American Chemical Society, 1996, 118, 7708-7715.
47. G. A. Olah, S. C. Narang, D. Meidar and G. F. Salem, Synthesis, 1981, 1981, 282-283.
48. F. Waller and R. W. Scoyoc, CHEMTECH, 1987, 17, 438-441.

Without further description, it is believed that one of ordinary skill in the art can, using the preceding description and illustrative examples, make, utilize and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The invention claimed is:

1. A solvent free method for separation and recovery of 2,3-butanediol (2,3-BDO) from fermentation broth, said process comprising the steps of:
   a) acetalization of fermentation broth with an aldehyde in the presence of a catalyst forming cyclic acetal; wherein the catalyst is selected from the group consisting of ZSM-5 with silicon/aluminum, Nafion NR50® and Amberlyst-15®;
   said step (a) conducted at a temperature that is selected from room temperature and about 40° C., for about 3-5 hours;
   b) isolating 2,3-BDO as phase-separated cyclic acetal; wherein the cyclic acetal is dioxolane;
   c) transacetalization of phase-separated dioxolane with methanol followed by distillation of acetal, to obtain high purity 2,3-BDO and butyraldehyde dimethyl acetal;
   d) distilling off butyraldehyde dimethyl acetal;
   e) recovering high purity 2,3-BDO; and
   f) recycling and reusing the catalyst; wherein the catalyst is reactive after about 10 cycles.

2. The method according to claim 1, wherein the catalyst is ZSM-5 with silicon/aluminum.

3. The method according to claim 1, wherein the aldehyde is selected from the group consisting of butanal, hexanal, octanal, 2-ethylbutanal and 2-ethyl hexanal.

4. The method according to claim 1, wherein the catalyst is selected from the group consisting of Nafion NR50® and Amberlyst-15®.

5. The method according to claim 4, wherein the amount of the catalyst is about 10% to about 30% by weight.

6. The method according to claim 1, wherein the fermentation broth is selected from the group consisting of aqueous butanediol, butanediol broth mimic and actual fermentation broths.

7. The method according to claim 6, wherein the fermentation broth comprises pure sugar and hydrolysate broth.

8. The method according to claim 1, wherein the isolation yield of pure 2,3-BDO is about 90%.

9. The method according to claim 1 wherein the catalyst performed at a conversion level of more than 95%.

10. The method according to claim 1 wherein the aldehyde employed is selected from butanal and hexanal.

11. The method according to claim 7 wherein the fermentation broth further comprises components selected from glucose, xylose, arabinose, acetoin, glycerol, xylitol, lactic acid, ethanol, and acetic acid.

12. An integrated solvent free method for separation and recovery of 2,3-butanediol (2,3-BDO) from fermentation broth, said process comprising the steps of:
   a) acetalization of fermentation broth with an aldehyde in the presence of a catalyst forming cyclic acetal; wherein the catalyst is selected from the group consisting of aluminum oxide, aluminum phosphate, ZSM-5 with silicon/aluminum, Nafion NR50® and Amberlyst-15®;
   b) isolating 2,3-BDO as phase-separated cyclic acetal; wherein the cyclic acetal is dioxolane;
   c) upgrading methyl ethyl ketone (MEK) synthesis by cleavage of dioxolane with a catalyst to form methyl ethyl ketone (MEK) and butanal;
   d) recycling butanal by adding the resulting product of MEK and butanal to the said fermentation broth.

13. The method according to claim 12, wherein the method was conducted in the presence of a catalyst selected from aluminum oxide, aluminum phosphate, and ZSM-5 with silicon/aluminum.

14. The method according to claim 12 wherein the catalyst is ZSM-5 with silicon/aluminum.

15. The method according to claim 12 wherein the catalyst is selected from the group consisting of Nafion NR50® and Amberlyst-15®.

16. The method according to claim 12 wherein the wherein the amount of the catalyst is about 50% by weight to about 60% by weight.

17. The method according to claim 14 wherein the catalyst is ZSM-5 with Si/Al: 80.

18. The method according to claim 13, wherein the amount of the catalyst is about 40% by weight to about 50% by weight.

19. The method according to claim 12, wherein step (c) of the method was conducted at a temperature of about 290° C. to about 325° C.

20. A solvent free method for separation and recovery of 2,3-butanediol (2,3-BDO) from fermentation broth, said process comprising the steps of:
   a) acetalization of fermentation broth with an aldehyde in the presence of a catalyst forming cyclic acetal; wherein the catalyst is selected from the group consisting of ZSM-5 with silicon/aluminum, Nafion NR50® and Amberlyst-15®;
   said step (a) conducted at a temperature that is selected from room temperature and about 40° C., for about 3-5 hours;
   a) isolating 2,3-BDO as phase-separated cyclic acetal; wherein the cyclic acetal is dioxolane;
   b) transacetalization of phase-separated dioxolane with methanol followed by distillation of acetal, to obtain high purity 2,3-BDO and butyraldehyde dimethyl acetal;
   c) distilling off butyraldehyde dimethyl acetal;
   d) recovering high purity 2,3-BDO;
   e) recycling and reusing the catalyst; wherein the catalyst is reactive after about 10 cycles;
   f) upgrading methyl ethyl ketone (MEK) synthesis by cleavage of dioxolane obtained from step (a) with an acid catalyst to form methyl ethyl ketone (MEK) and butanal; and
   g) recycling butanal by adding the resulting product of MEK and butanal to the said fermentation broth.

* * * * *